United States Patent
Miller

(12) 
(10) Patent No.: US 8,287,187 B2
(45) Date of Patent: Oct. 16, 2012

(54) ADJUSTABLE DYNAMIC X-RAY FILTER

(76) Inventor: Zachary A. Miller, San Francisco, CA (US)

(*) Notice: Subject to any disclaimer, the term of this patent is extended or adjusted under 35 U.S.C. 154(b) by 198 days.

(21) Appl. No.: 12/819,267

(22) Filed: Jun. 21, 2010

(65) Prior Publication Data

US 2011/0311032 A1    Dec. 22, 2011

(51) Int. Cl.
*A61B 6/08* (2006.01)
(52) U.S. Cl. .................................. 378/205; 378/154
(58) Field of Classification Search .................. 378/205, 378/206, 154, 155
See application file for complete search history.

(56) References Cited

U.S. PATENT DOCUMENTS

| | | | |
|---|---|---|---|
| 4,532,646 A | 7/1985 | Gilbert | |
| 5,008,920 A | 4/1991 | Gralak | |
| 5,241,578 A | 8/1993 | MacMahon | |
| 5,388,143 A | 2/1995 | MacMahon | |
| 5,772,574 A | 6/1998 | Nanko | |
| 5,781,610 A | 7/1998 | Miles | |
| 6,206,566 B1 * | 3/2001 | Schuetz | 378/205 |
| 6,438,211 B1 | 8/2002 | Weekamp et al. | |
| 6,702,459 B2 | 3/2004 | Barnes et al. | |
| 6,893,157 B2 * | 5/2005 | Arakawa | 378/205 |
| 7,147,371 B2 | 12/2006 | Hecker | |
| 7,344,304 B2 | 3/2008 | Hardesty | |
| 7,581,884 B1 | 9/2009 | Barnes et al. | |
| 2002/0080922 A1 | 6/2002 | Kwasnick et al. | |
| 2002/0150215 A1 | 10/2002 | Barnes et al. | |
| 2002/0168052 A1 | 11/2002 | Castleberry | |
| 2004/0028181 A1 | 2/2004 | Charles, Jr. et al. | |
| 2006/0023832 A1 | 2/2006 | Edic et al. | |
| 2006/0256917 A1 | 11/2006 | Jacobs et al. | |
| 2007/0104321 A1 | 5/2007 | Spahn | |
| 2008/0130837 A1 | 6/2008 | Heath et al. | |
| 2008/0240357 A1 | 10/2008 | Jabri et al. | |

OTHER PUBLICATIONS

PCT Search Report, Oct. 5, 2011, pp. 1-8, International Searching Authority, US.

* cited by examiner

*Primary Examiner* — Hoon Song
(74) *Attorney, Agent, or Firm* — Keith D. Nowak; Carter Ledyard & Milburn LLP

(57) ABSTRACT

A system and method for determining the location of an x-ray source of an x-ray machine and adjusting grid lines in an anti-scatter grid are disclosed. An ideal beam path is obtained and is used to adjust grid lines in the anti-scatter grid. In one embodiment, the invention uses a source locator to locate the x-ray source, communicate this location to the said adjustable anti-scatter grid which could align the grid lines mechanically, by means of servos attached to the grid lines, to the ideal x-ray beam path. In other embodiment electrical currents are used to align grid lines with the beam source. By aligning the grid lines with the beam path, images with increased contrast and reduced noise can be produced.

7 Claims, 8 Drawing Sheets

ADJUSTABLE DYNAMIC X-RAY FILTER

PRIORITY AND RELATED APPLICATION

N/A

FIELD OF THE INVENTION

The present invention relates to x-ray imaging, in particular, to alignment systems for portable x-ray imaging devices.

BACKGROUND OF THE INVENTION

In a hospital setting, mobile radiographic exams are performed on patients that are incapable of being moved, or are difficult to move. In tertiary care medical centers, mobile radiographic exams represent a significant percentage of the radiographic exams performed. X-rays passing through an object, such as a human body, experience some degree of scatter. The primary x-rays transmitted through an object travel on a straight line path from the x-ray source (also referred to herein as the x-ray focal spot) to the image receptor and carry object density information. Scattered x-rays form a diffuse image that degrades primary x-ray image contrast. In some patients, scattered x-ray intensity exceeds the intensity of primary x-rays. Scattering phenomena is well known and routinely compensated for in general radiography, fluoroscopy and mammography through the use of anti-scatter grids.

An anti-scatter grid is generally formed from alternating strips of x-ray opaque (or radiopaque) material and x-ray transmissive (or radiolucent) material. Lead may be used as the x-ray opaque material and plastics, aluminum or fiber may be used as the x-ray transmissive material. The grid is positioned between the object of interest and the x-ray image receptor plate and oriented such that the image forming primary x-rays are incident only with the edges of the x-ray opaque material. Thus, the majority of primary x-rays pass through the radiolucent spacer strips. In contrast, scattered x-rays are emitted in all directions after interaction with the target object and as such, scattered x-rays are incident on a larger area of the lead strips and only a small percentage of scattered x-rays are transmitted by the grid, as compared to primary x-rays.

The degree of scatter control for a given grid depends upon the grid ratio, which is defined as the ratio of the radiopaque strip thickness in the direction of the x-ray path to the width of the radiolucent spacer material as measured orthogonal to the x-ray beam path. Thus, the higher the grid ratio, the greater the scatter control. A high grid ratio, while more effective, is also more difficult to align relative to a focal spot. In order to compensate for x-ray beam divergence in a focused grid, the radiopaque strips are tilted to a greater extent with increasing distance from the center of the grid. The planes of the grid vanes all converge along a line known as the focal line. The distance from the focal line to the surface of the grid is referred to as the focal length of the grid. The focal line coincides with the straight line path to the focal spot. Thus, when the focal spot is coincident with the focal line of the grid, the primary x-rays have minimal interaction with the radiopaque lead strips and maximal primary transmission is obtained. Misalignment of the focal line of the anti-scatter grid with the focal spot diminishes primary x-ray transmission while scattered x-ray transmission remains unchanged. Thus, optimal primary x-ray transmission requires alignment (positional and orientational) of the focal spot with the focal line of the anti-scatter grid.

In general radiography, fluoroscopy and mammography, the image receptor and x-ray tube are rigidly mounted and in a fixed position relative to one another, thereby making focal spot and grid alignment a simple process. In mobile radiography, an image receptor is placed under a bedridden patient and the x-ray source is positioned above the patient. Since the relative separation of the focal spot and the image receptor is variable, determining the proper position and orientation of an anti-scatter grid between a patient and the image receptor becomes a difficult alignment problem. If a grid is not used, only a small fraction of the possible contrast is obtained in the x-ray image.

When grids are utilized in conjunction with mobile radiography, the grid is typically not aligned. Misalignment problems are diminished by utilizing a grid having a low ratio of 8:1 or less. Although x-ray image contrast is improved with the use of a low ratio grid, the contrast remains significantly lower than otherwise could be obtained with a properly aligned, high ratio grid having a grid ratio of 10:1 or greater.

Thus while mobile radiography is in many ways more convenient than fixed installation radiography, its clinical utility is diminished due to the inferior image quality caused by scattered radiation. This is a greater problem in mobile radiography due to the difficulty in producing the proper alignment of the focal spot with the anti-scattering grids. A means to produce proper alignment that is easy for the operator to use would significantly improve mobile radiographic image contrast and image quality, and thus increase the clinical utility of mobile radiography.

SUMMARY OF THE INVENTION

A system and method for determining the location of an x-ray source of an x-ray machine and for adjusting grid lines in an anti-scatter grid are disclosed. In one embodiment, the invention uses a source locator in conjunction with an infrared (IR) transmitter and IR receiver to locate the x-ray source and to align grid lines with an ideal x-ray beam path. By aligning the grid lines with the beam path, images with increased contrast and reduced noise can be produced.

The present invention provides a system for determining location of an x-ray source of an x-ray machine such as a portable x-ray machine. The system includes an x-ray source and a source locator. The x-ray source emits x-ray beams which have an idealized beam path. The source locator is associated with the x-ray source and has an IR transmitter. The IR transmitter of the source locator transmits location information defining the location of the x-ray source with the location information being generated by the source locator. The system may further comprise an x-ray grid having an IR receiver and x-ray grid lines that adjust to the emitted x-ray beams. The grid lines selectively permit the emitted x-ray beams to pass through said x-ray grid and align with the idealized path of the emitted x-ray beams. The grid lines adjust to the idealized beam path and selectively permit the emitted x-ray beams to pass through the x-ray grid in response to the IR emissions received by the IR receiver.

The present invention also provides a system for obtaining x-ray images with increased contrast and reduced noise. The system includes an x-ray beam source and an adjustable x-ray grid. The x-ray beam source emits x-ray beams and has a source locator associated therewith for determining the location of the x-ray source. The x-ray grid includes a plurality of grid lines comprising alternating radiopaque and radiolucent material. The grid lines of the x-ray grid may be adjusted to said x-ray beam source using an electromagnetic field, a servo motor or other computer driven mechanisms. The grid lines may be adjusted between a first unobstructed position that permits x-ray beam emissions to pass through the grid, and a second obstructed position that prohibits x-ray beam emissions from passing through the grid. The grid lines may comprise strips of material or individual radiolucent spheres with radiopaque material disposed in a central plane of each radiolucent sphere. The radiolucent material has a first charged side and a second charged side, where said first charged side is an opposite charge from said second charged side.

The present invention further provides a method of adjusting grid lines in an anti-scatter grid by providing an x-ray source, providing an adjustable x-ray grid and adjusting said x-ray grid lines to align with x-ray beam emissions of said x-ray source. In one embodiment radiolucent spheres include a layer of radiopaque material disposed in a central plane of each sphere. The adjustment means selectively align said x-ray grid lines to permit passage of said x-ray beam emissions through said x-ray grid. The adjustment means also includes use of a computer that receives location information obtained by the source locator to selectively align said x-ray grid lines to an idealized path of said x-ray beam emissions and to permit passage of said x-ray beam emissions through said x-ray grid.

DETAILED DESCRIPTION OF THE INVENTION

Figure 1:
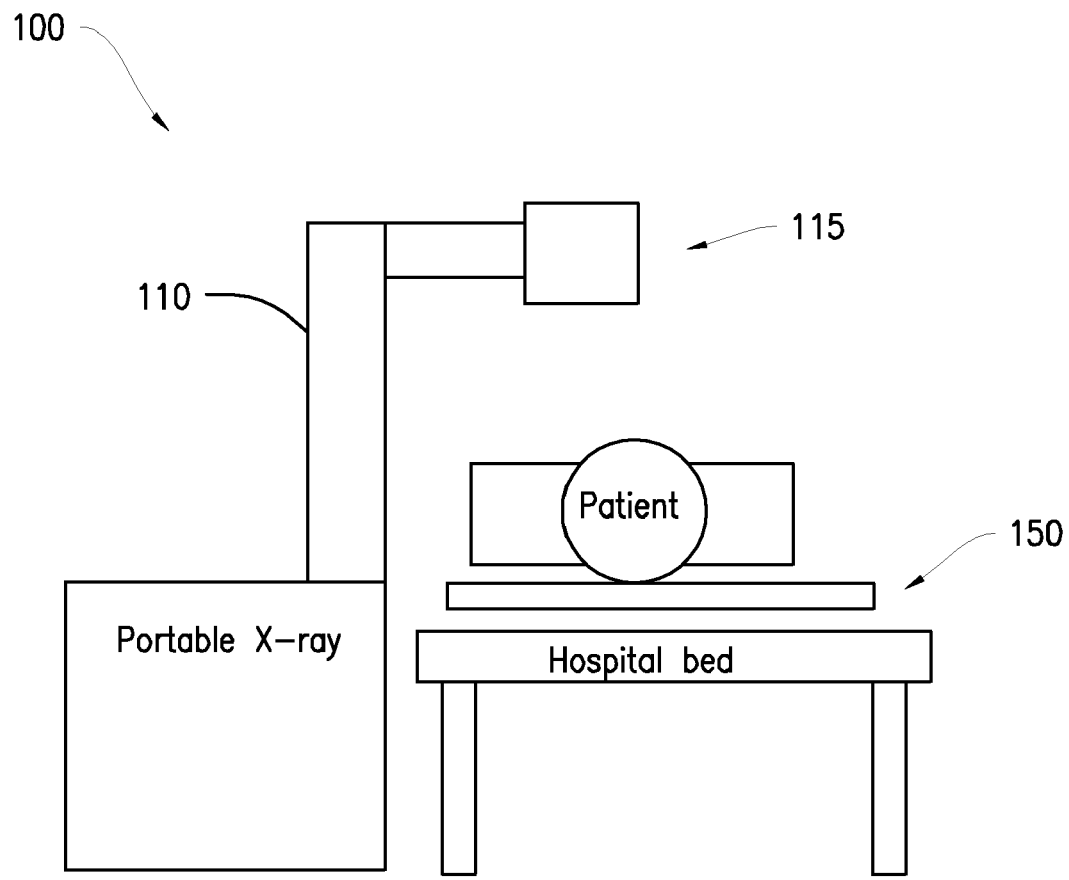
FIG. 1 is an illustration of a portable x-ray apparatus according to the present invention.
Figure 3:
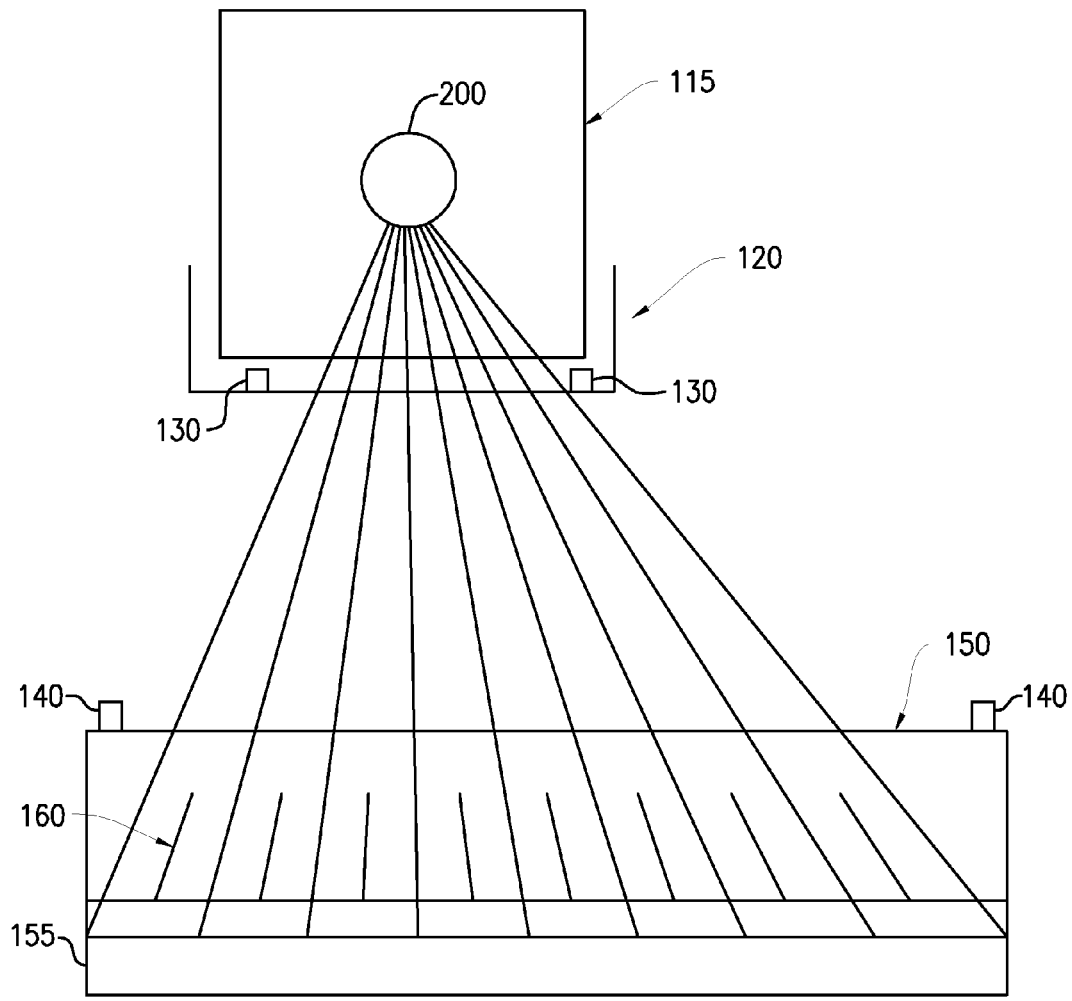
FIG. 3 is an embodiment of an x-ray plate employed in FIG. 1.

FIGS. 1 and 3 show a system 100 of the present invention for aligning x-ray emissions from an x-ray machine and for adjusting grid lines in an anti-scatter grid to obtain diagnostic image information with increased contrast and reduced noise due to scattered x-rays. The system 100 includes a portable x-ray machine 110 having an x-ray head 115 and an x-ray plate 150 used to removably receive an x-ray film cassette or digital x-ray detector 155. In one embodiment, a source locator 120 is attached to the housing of x-ray head 115 of x-ray machine 110 and x-ray plate 150 is attached to a flexible filter, anti-scatter grid 160. Both the source locator 120 and the flexible filter, anti-scatter grid 160 are mechanisms used to facilitate the acquisition of images with increased contrast and reduced noise when compared to images obtained using prior art portable x-ray machines and prior art grids.

Figure 2A:
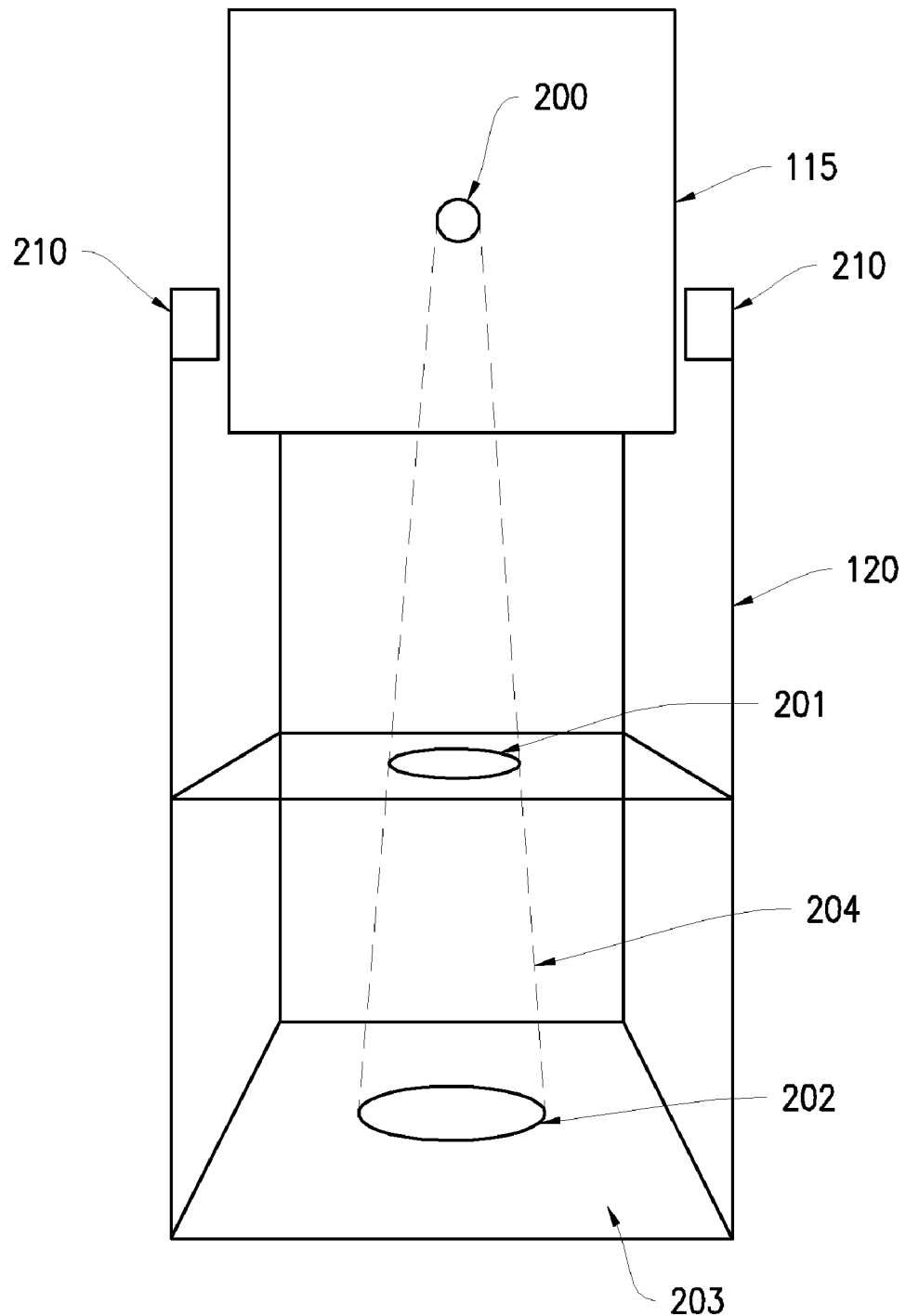
FIGS. 2A and 2D are illustrations of a source locator disposed on an x-ray source of the portable x-ray apparatus according to FIG. 1.

Referring now to FIG. 2A, there is shown a source locator 120 in greater detail. The purpose of source locator 120 is to determine the location of the x-ray source 200, and to record that location information in an appropriate digital storage device. The digital storage device is then associated with circuitry affixed to x-ray head 115 so that once the source locator is removed, or the x-ray head itself is moved, the location of the x-ray source in a particular x-ray head is stored and accurately known at all times.

Shown in FIG. 2A is x-ray source 200, the location of which must be determined, x-ray opaque object 201 and an image 202 of the x-ray opaque recorded on film 203. As described below, determination of the size differences between object 201 and image 202, along with appropriate computer calculations based on these differences, allow a precise determination of the x-ray source location. When the mobile x-ray machine is turned on x-ray radiation 204 is generated which passes over object 201 and is recorded on film 203 as image 202. As object 201 is x-ray opaque, the size of image 202 will vary based on the relative locations of x-ray source 200, object 201 and image 202.

Figure 2B:
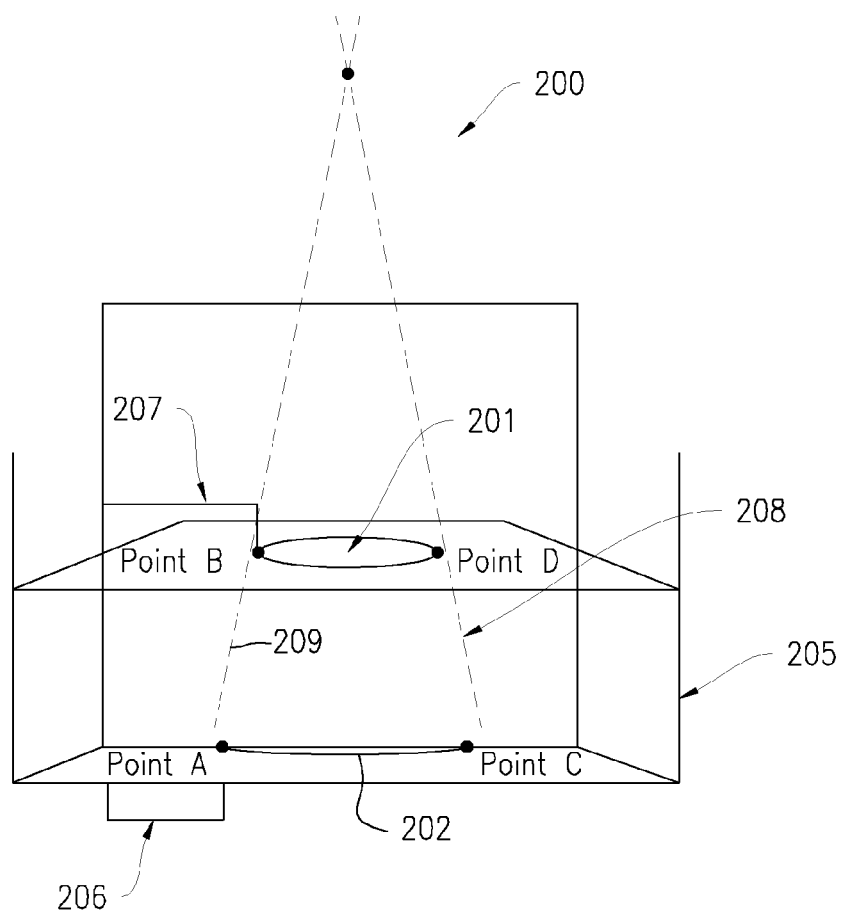

Referring now to FIG. 2B, there is shown the manner in which the location of the x-ray source can be calculated. More particularly, the location coordinates of Points A and C are known as the "Y" dimension (distance 205) is known and fixed. Similarly distance 207 is known, so that the locations of Points B and D are known but distance 206 is variable and not known. Using known techniques, the difference in size between object 201 and image 202 can be readily determined.

Figure 2C:
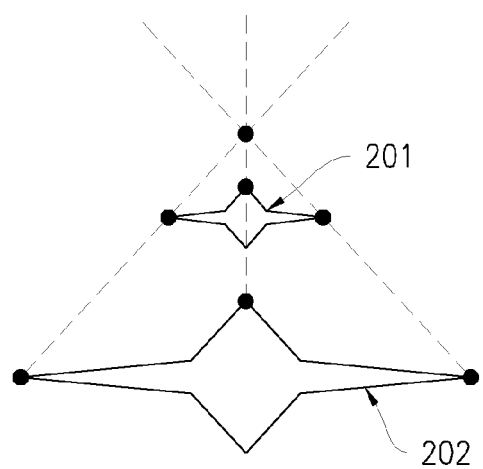

Knowing the location of Points D and C it is possible to calculate the relative angle of line 208 and knowing that angle it is possible to calculate the correct angle of line 209. The extension of lines 208 and 209 can be calculated to determine the precise location of x-ray source 200. It is to be understood that the known calculations described above would be accomplished on a computing device (not shown) associated with source locator 120. FIG. 2C illustrates the use of a star-shaped object 201, which represents an example of a figure with more distinct visual landmarks than the disc 201 shown in FIG. 2B, which may be employed to simplify the needed calculations.

Figure 2D:
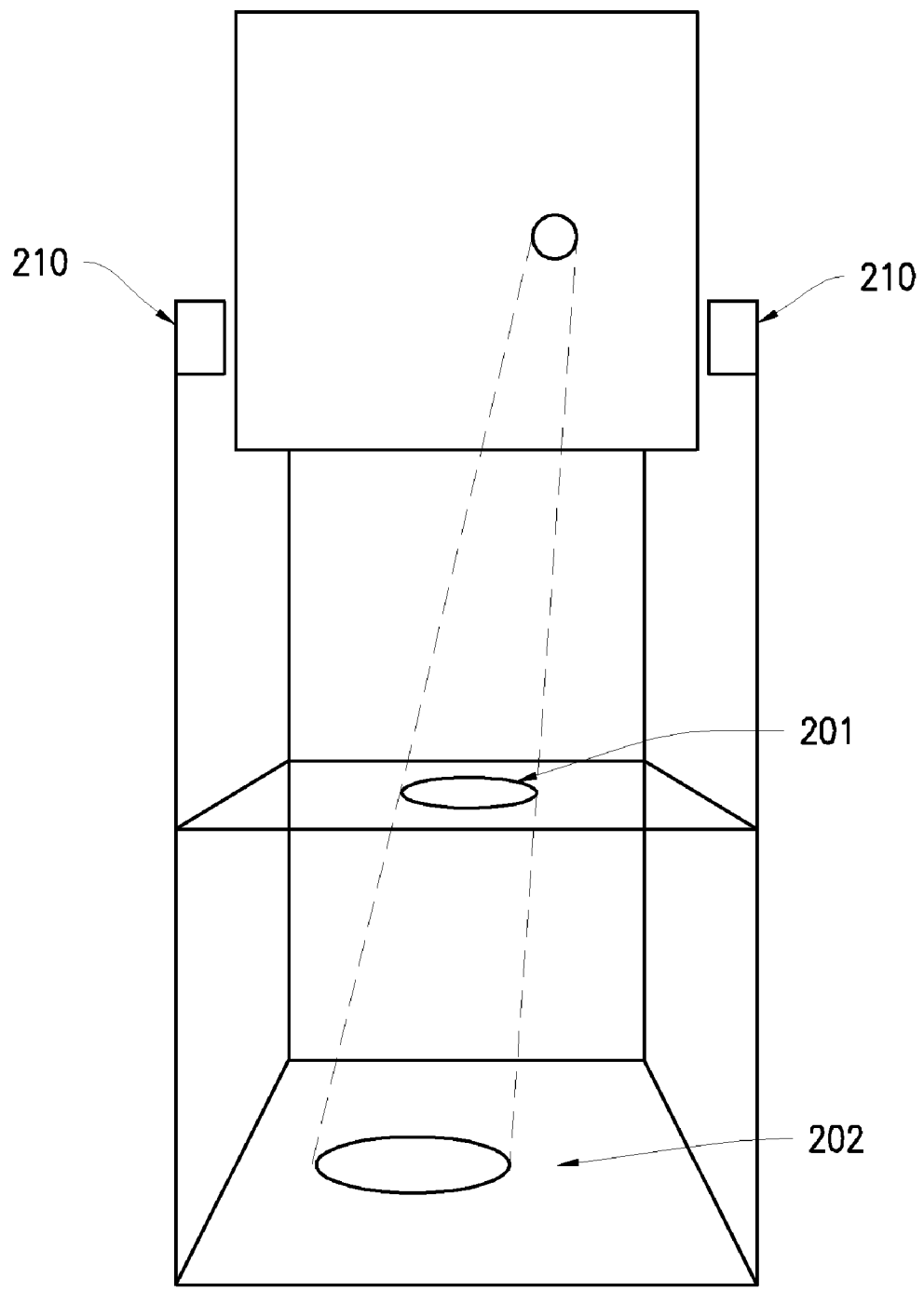

FIG. 2D shows an example where the x-ray is off center but the same process described above can be used to calculate its precise location. FIG. 2D also illustrates a representation of the digital storage device 210 described above in which the location information for x-ray source 200 is stored.

Referring specifically to FIG. 3, the source locator 120 is disposed on, integrated with or removably attachable to the x-ray head 115 of the x-ray machine 110. The locator 120 is used to determine the location of the actual x-ray focal spot 200 of the portable x-ray machine 110 as described above. The source locator 120 has, for example, infra red (IR) transmitters 130 disposed thereon and x-ray plate 150 has, for example an IR receiver 140 disposed thereon. The IR transmissions from transmitter 130 are received by IR receiver 140 in order to transmit the location of the x-ray source 200. It is understood that the location of the x-ray source 200 is stored in digital device 210, which stored information is used by IR transmitter 130. The general concept of using an IR transmitter and an IR receiver to transmit the location of a particular object is known. See for example U.S. Pat. No. 5,627,524. This system or similar known techniques can be used in accordance with the present invention.

After the location of x-ray source 200 has been determined and grid 160 adjusted as described below, source locator 120 can be removed from x-ray head 115. However the location of x-ray source 200 remains stored in digital storage device 210 so that the location of source 200 is available for subsequent use of the portable x-ray machine.

Figure 4:
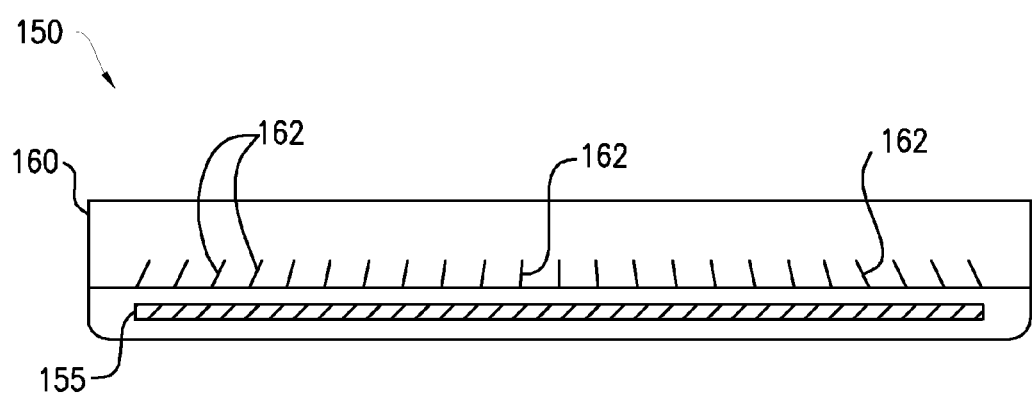
FIG. 4 is another embodiment of an x-ray plate employed in FIG. 1.

Referring now to FIG. 4, an embodiment of the x-ray plate 150 is shown. In one embodiment, the flexible filter, anti-scatter grid 160 is attached to the x-ray plate 150 that is used to removably receive detector 155. In other embodiments, the grid 160 may be removably attached to the x-ray plate 150. In use, the x-ray plate 150 would be oriented so that a patient would be situated on top of the grid 160 of the plate 150 with the detector 155 being disposed therebelow. The grid 160 reduces the effect of scattering by preventing scattered x-rays from reaching the detector 155.

The detector 155 may include an x-ray photosensitive film or a digital x-ray detector. For example, a suitable digital detector may include a cesium iodide phosphor (scintillator) on an amorphous silicon transistor-photodiode array having a pixel pitch of about 100 micrometers. Other suitable detectors may include a charge-coupled device (CCD) or a direct digital detector which converts x-rays directly to digital signals. While the photosensitive film is illustrated as being flat and defining a flat image plane, other configurations of the photosensitive film and digital detectors may be suitably employed, e.g., a curved-shaped photosensitive film or digital detector having a curved image plane.

Still referring to FIG. 4, the grid 160 has adjustable and dynamic grid lines 162 that are adjusted in response to the location of the x-ray focal spot as determined by source locator 112. This creates an idealized beam path of the x-ray emissions from the x-ray source 200. The grid 160 communicates with the source locator 120 via the IR transmitters and receivers described above in order to determine the idealized path of x-ray beams and then, based on the idealized path, the grid lines 162 adjust to line up with the idealized path. The grid lines 162 comprise a set of individual strips of radiopaque material and a set of individual strips of radiolucent material as described above.

In one embodiment, the radio-opaque material of the grid lines 162 comprise parallel lead louvers that employ servo motors to adjust the lead louvers based on the calculated idealized path. In this embodiment, a computer system may be used to obtain the idealized path information from the source locator, calculate the location of the focal spot and then adjust the louvers using the servo motor.

Figure 5A:
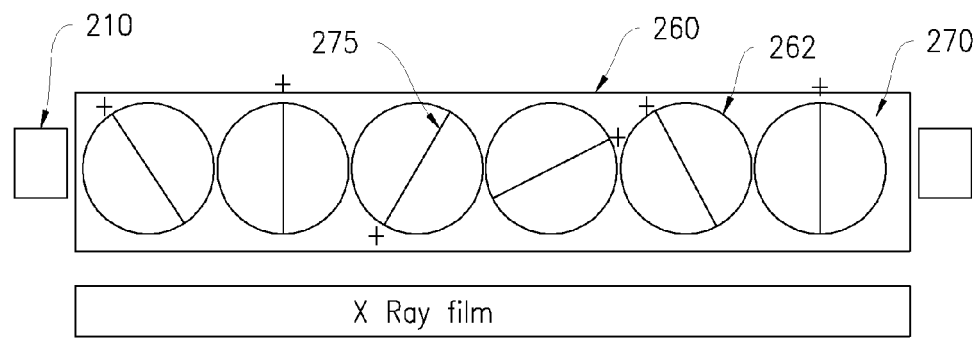
FIGS. 5A-5C illustrate the use of radiolucent spheres as embodiments of an x-ray grid.
Figure 5B:
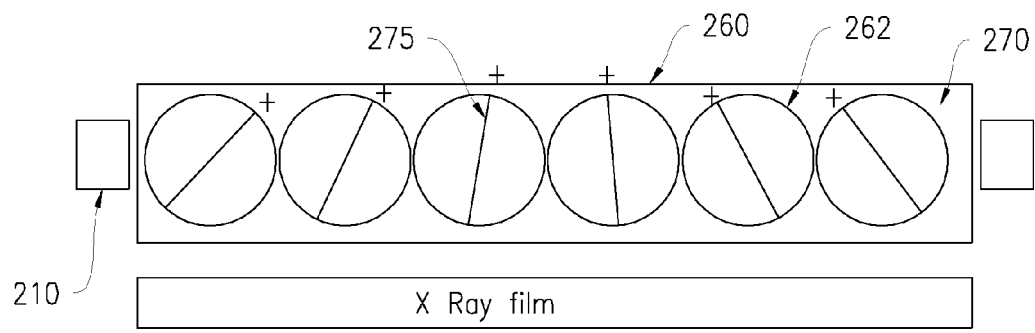
Figure 5C:
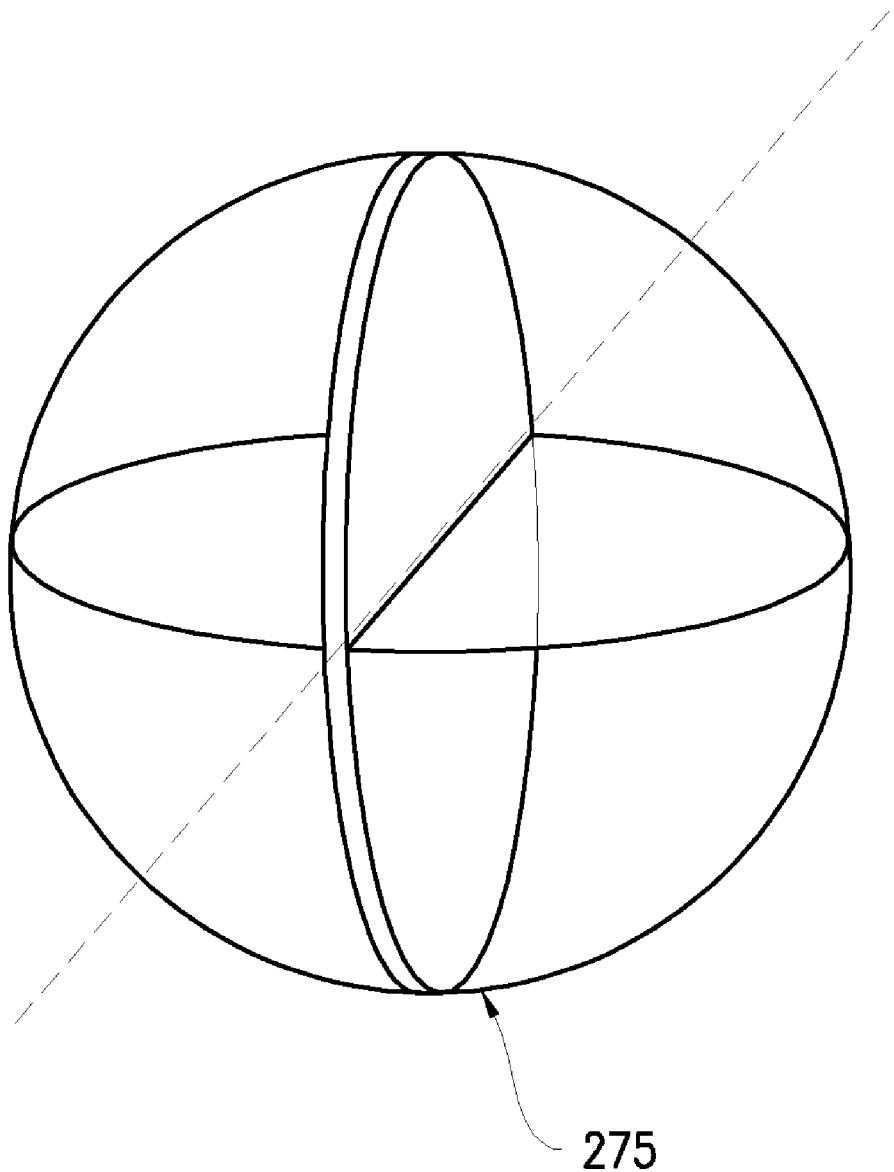

FIG. 5A shows another embodiment of x-ray plate 150 that comprises a grid 260 formed of grid lines taking the form of spheres 262 floating in a fluid matrix. The grid 260 would be part of a fluid system where the spheres 262 exist in one plane, or planar system. The spheres 262 may be suspended in any type of fluid or semi-fluid radiolucent material 270. Each sphere 262 has a plane of radio-opaque material 275 disposed therein. For instance, each sphere 262 has a thin layer of lead or similar radio-opaque material 275 that cuts through the sphere 262 in the center plane 275. Each sphere 262 would have the same polarity so that each center plane of each sphere 262 would align in response to the application of an appropriate electromagnetic field. When the idealized x-ray path is determined, as described above the control computer would apply an electromagnetic field to the planar system of the grid 260 so the lead plane 275 of the each sphere 262 aligns to the idealized path emitted from the x-ray source 200. By using an electromagnetic field, the spheres 262 are selectively adjusted to obstruct or permit x-ray beam emissions from the x-ray source 200. FIG. 5B illustrates one specific alignment of spheres 262 and FIG. 5C illustrates a sphere 262 having more than one plane, specifically two planes in this case, which may increase the performance of the anti scatter grid.

While the present invention has been described in conjunction with specific embodiments, those of normal skill in the art will appreciate the modifications and variations can be made without departing from the scope and the spirit of the present invention. Such modifications and variations are envisioned to be within the scope of the appended claims.

The invention claimed is:

1. A system for determining the location of an x-ray source of an x-ray machine comprising:
    an x-ray source, said x-ray source emitting x-ray beams, said emitted x-ray beams having an idealized beam path, said x-ray source having a source locator associated therewith, said source locator including an IR transmitter;
    a computing device for determining a location of the x-ray source based on determining size differences between an x-ray opaque object and an image of the x-ray opaque object;
    a digital storage device for storing location results derived from the computing device; and
    an x-ray grid having x-ray grid lines, said x-ray grid lines adjusting to said idealized beam path of said x-ray beam source in response to the location information transmitted to the IR transmitter to selectively permit said emitted x-ray beams to pass through said x-ray grid,
    wherein the location information stored in the digital storage device is transmitted by the IR transmitter.

2. The system of claim 1, wherein said x-ray source is a portable x-ray machine.

3. A system for obtaining x-ray images with increased contrast and reduced noise including an x-ray beam source, said beam source emitting x-ray beams, said emitted x-ray beams having an idealized beam path, said x-ray source having a source locator associated therewith, said source locator including an IR transmitter associated therewith, said system further including an adjustable x-ray grid, said system further comprising:
    a plurality of grid lines included in said x-ray grid, said plurality of grid lines comprising radiopaque material;
    a computing device included as part of the source locator for generating location information which specifies the location of the x-ray source based on the relative positions of an x-ray opaque object and an image of the x-ray opaque object;
    an adjustment mechanism responsive to said location information for adjusting said grid lines so that said grid lines align with said x-ray beam emissions from said x-ray beam source in a first position; and
    wherein said grid lines of said adjustable x-ray grid obstruct said x-ray beam emissions from said x-ray beam source in a second position.

4. The system of claim 3, wherein said plurality of grid lines further comprise radiolucent material, said radiopaque material alternating with said radiolucent material.

5. The system of claim 4, wherein said radiolucent material of said plurality of grid lines comprise individual radiolucent spheres and said radiopaque material being disposed in a central plane of each of said radiolucent spheres.

6. The system of claim 5, wherein said radiopaque material has a first magnetic charged side and a second magnetic charged side, said first magnetic charged side being an opposite magnetic charge from said second magnetic charge side.

7. A method of adjusting grid lines in an anti-scatter grid comprising:
    providing an x-ray source, said x-ray source emitting x-ray beams, said x-ray source having a source locator associated therewith, said source locator including an IR transmitter, said source locator provides location information to specify the location of the x-ray source;
    providing a stationary x-ray plate including an adjustable x-ray grid having x-ray grid lines and an IR receiver; and
    adjusting said x-ray grid lines to said x-ray beam emissions of said x-ray beam source in response to said location information, wherein said location information includes information about transmissions from said IR transmitter that are received by said IR receiver.

* * * * *